United States Patent
Nishio et al.

(10) Patent No.: US 12,114,886 B2
(45) Date of Patent: Oct. 15, 2024

(54) MEDICAL DEVICE AND METHOD

(71) Applicant: TERUMO KABUSHIKI KAISHA, Tokyo (JP)

(72) Inventors: Kosuke Nishio, Kanagawa (JP); Junichi Kobayashi, Kanagawa (JP); Tomonori Hatta, Kanagawa (JP); Taiga Nakano, Kanagawa (JP)

(73) Assignee: TERUMO KABUSHIKI KAISHA, Tokyo (JP)

(*) Notice: Subject to any disclaimer, the term of this patent is extended or adjusted under 35 U.S.C. 154(b) by 817 days.

(21) Appl. No.: 16/926,893

(22) Filed: Jul. 13, 2020

(65) Prior Publication Data

US 2020/0337720 A1 Oct. 29, 2020

Related U.S. Application Data

(62) Division of application No. 15/610,320, filed on May 31, 2017, now Pat. No. 10,786,278.

(51) Int. Cl.
*A61B 17/3207* (2006.01)
*A61B 17/32* (2006.01)
(Continued)

(52) U.S. Cl.
CPC ........ *A61B 17/320758* (2013.01); *A61B 17/32002* (2013.01); *A61B 17/3207* (2013.01);
(Continued)

(58) Field of Classification Search
CPC ...... A61B 17/320758; A61B 17/32002; A61B 17/3207; A61B 2017/00845;
(Continued)

(56) References Cited

U.S. PATENT DOCUMENTS 4,728,319 A * 3/1988 Masch ............ A61B 18/1442
606/177
5,314,438 A * 5/1994 Shturman ......... A61M 25/01
606/159
(Continued)

FOREIGN PATENT DOCUMENTS

| CN | 101511284 A | 8/2009 |
| CN | 103200886 A | 7/2013 |
| EP | 1 459 705 A1 | 9/2004 |

OTHER PUBLICATIONS

Office Action (The First Office Action) issued Mar. 9, 2022, by the State Intellectual Property Office of People's Republic of China in corresponding Chinese Patent Application No. 201880030794.2 and an English Translation of the Office Action. (25 pages).

(Continued)

*Primary Examiner* — Ashley L Fishback
*Assistant Examiner* — Chima U Igboko
(74) *Attorney, Agent, or Firm* — BUCHANAN INGERSOLL & ROONEY PC

(57) ABSTRACT

A medical device for grinding substance inside a body lumen includes a rotatable tubular drive shaft, a treatment member connected to the drive shaft, and a tubular member possessing an axially extending lumen that extends throughout the tubular member. The tubular member is mounted on the treatment member and surrounds a portion of the treatment member so that the treatment member is rotatable relative to the tubular member. The treatment member includes a shearing portion, and the tubular member includes a protrusion that projects toward the lumen of the tubular member. The protrusion is located axially in front of the shearing portion and interacts with the shearing portion (Continued)

during relative rotation between the treatment member and the tubular member to shear debris resulting from the grinding of the substance.

20 Claims, 12 Drawing Sheets

(51) Int. Cl.
*A61B 17/00* (2006.01)
*A61B 17/22* (2006.01)

(52) U.S. Cl.
CPC ............... *A61B 2017/00845* (2013.01); *A61B 2017/22038* (2013.01); *A61B 2017/320032* (2013.01)

(58) Field of Classification Search
CPC ......... A61B 2017/22038; A61B 2017/320032; A61B 2217/005
See application file for complete search history.

(56) References Cited

U.S. PATENT DOCUMENTS

| | | | |
|---|---|---|---|
| 5,318,576 A | * | 6/1994 | Plassche, Jr. .. A61B 17/320725 606/159 |
| 6,126,667 A | | 10/2000 | Barry et al. |
| 6,565,588 B1 | | 5/2003 | Clement et al. |
| 2008/0004643 A1 | | 1/2008 | To et al. |
| 2010/0312223 A1 | | 12/2010 | Kozak et al. |
| 2012/0109171 A1 | | 5/2012 | Zeroni et al. |
| 2016/0157886 A1 | | 6/2016 | WasDyke et al. |
| 2016/0278805 A1 | | 9/2016 | Hatta et al. |
| 2018/0344347 A1 | | 12/2018 | Nishio |
| 2018/0344348 A1 | | 12/2018 | Nishio et al. |

OTHER PUBLICATIONS

Four known atherectomy devices available as of Dec. 14, 2016: 1) "Diamondback" sold by Cardiovascular Systems, Inc.; 1) "Phoenix" sold by Volcano (Philips); 3) "Rotoblator" sold by Boston Scientific; and 4) "Jetstream" sold by Boston Scientific, 1 Page.

\* cited by examiner

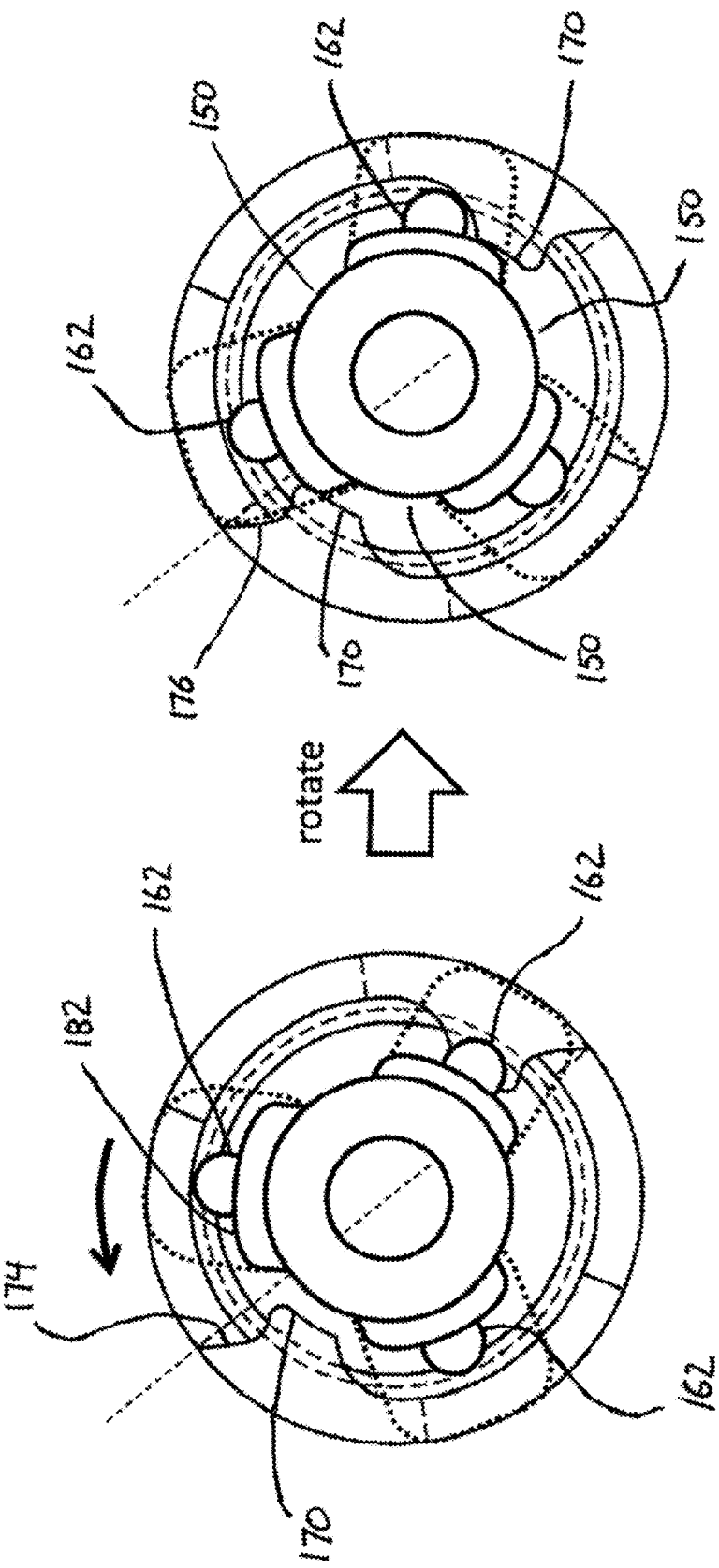

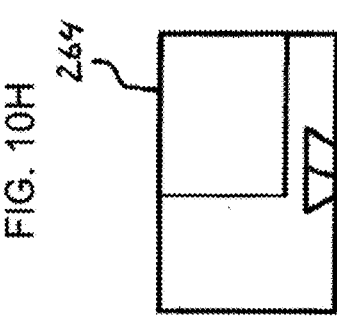
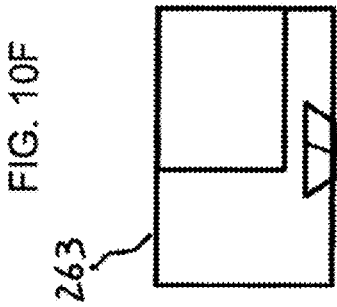
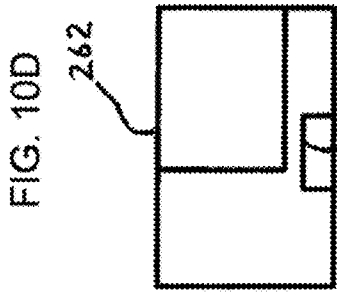
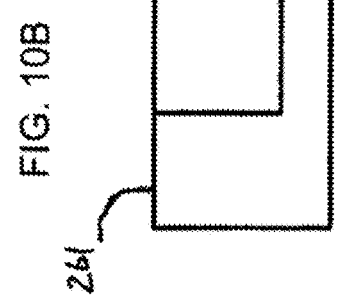
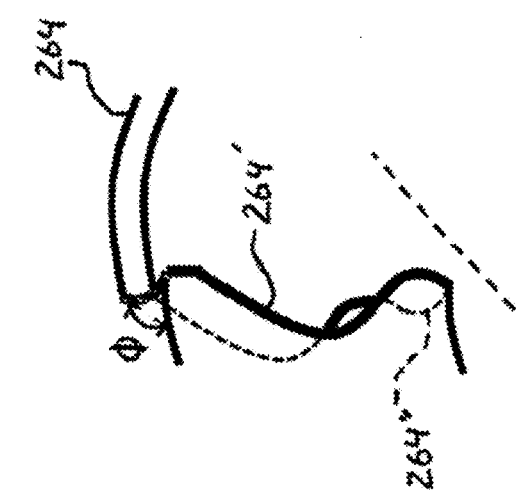
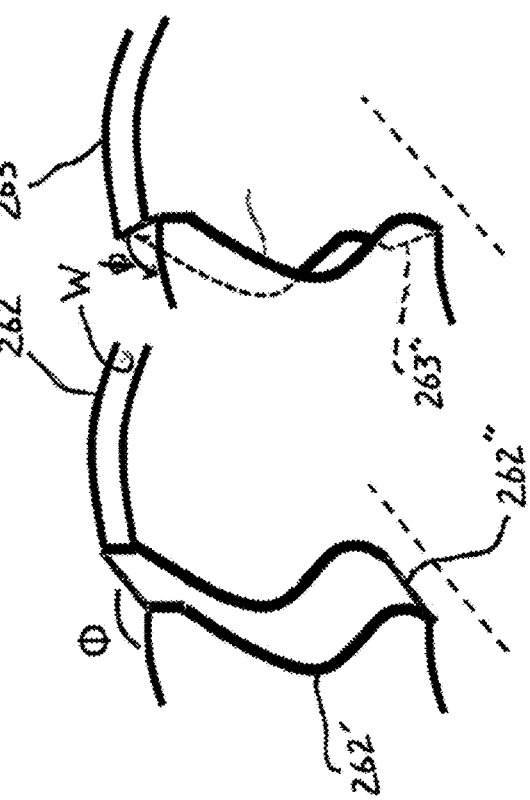
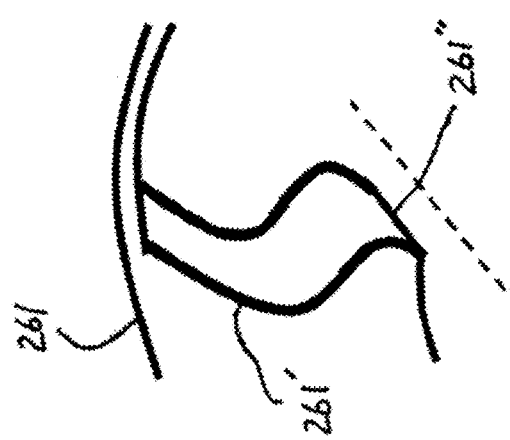

MEDICAL DEVICE AND METHOD

CROSS-REFERENCES TO RELATED APPLICATIONS

This application is a divisional of U.S. patent application Ser. No. 15/610,320 filed on May 31, 2017, the entire content of which is incorporated herein by reference.

TECHNICAL FIELD

The present invention generally relates to medical devices and methods for removing substances from a living body. More specifically, the present invention involves positioning a rotatable treatment member in a living body and grinding substance in the living body through rotation of the treatment member.

BACKGROUND DISCUSSION

Medical devices are used to remove substances from a living body. As an example, an atherectomy device is used to remove arteriosclerosis from a blood vessel. The atherectomy device is typically configured to be positioned in the living body adjacent the substance to be ground and then the treatment part of the device is then rotated to grind the substance. The debris resulting from this grinding procedure is then removed from the living body. The removal of the ground-away debris can be accomplished by way of a gateway lumen passing through the atherectomy device.

Experience has shown that these known devices and methods can result in distal embolization. That is, some of the debris can create an obstruction or blockage resulting in slow flow or no flow in the peripheral vessel. When this occurs, physicians must aspirate the peripheral vessel to remove the debris forming the distal embolization. In very severe cases, it may be necessary to perform amputation.

Proposals have been made to address concerns about distal embolization. For example, some atherectomy devices are provided with an aspiration function for removing the debris by way of an aspiration port. But these solutions have not been found to be particularly satisfactory. In some instances, choking of the aspiration port occurs, thus inhibiting or preventing a continuous aspiration of the desired region.

The atherectomy procedure for grinding substance from a living body lumen (removing arteriosclerosis from a blood vessel) typically involves the use of two different guidewires. A first coated guidewire is used to deliver the atherectomy device to the stenotic region or treatment area. After the atherectomy device is located at the desired position, the coated guidewire is removed and a second different guidewire is inserted into the atherectomy device. One way in which the second guidewire differs from the first is that the second guidewire is not coated. This second non-coated guidewire is used during operation of the atherectomy device when the treatment part is rotated at a high speed.

The reason two different guidewires are used is that the coated first guidewire is a preferred guidewire for guiding and delivering the atherectomy device to the treatment area. But the coating on this first guidewire tends to become abraded or damaged during rotation of the treatment part. The abrasion of the rotating treatment part against the coated guidewire can produce coating fragments that may cause distal embolization.

SUMMARY

According to one aspect, a medical device for treating a stenotic region in a body lumen in a living body comprises a rotatable tubular drive shaft, a treatment member, and an inner tubular member. The treatment member is positionable in the body lumen in the living body adjacent the stenotic region and possesses an outer grinding surface for grinding the stenotic region in the body lumen in the living body. The treatment member is connected to the drive shaft so that rotation of the drive shaft results in rotation of the treatment member, and the rotation of the treatment member causing the outer grinding surface of the treatment member to grind the stenotic region in the body lumen in the living body. The treatment member rotates together with the rotatable tubular drive shaft and includes an axially extending lumen that extends throughout the axial extent of the treatment member. The inner tubular member possesses oppositely located distal-most and proximal-most ends, and also includes an axially extending lumen that extends throughout an axial extent of the inner tubular member so that the lumen opens to the distal end-most of the inner tubular member and to the proximal-most end of the inner tubular member to permit passage of a guidewire. At least a distal part of the inner tubular member is positioned in the lumen of the treatment member. The treatment member and the inner tubular member are relatively rotatable, and the inner tubular member includes an enlarged diameter portion that is enlarged relative to an axially adjacent part of the inner tubular member. A portion of the lumen in the treatment member possesses an inner diameter smaller than the outer diameter of the enlarged diameter portion of the inner tubular member, and the enlarged diameter portion of the inner tubular member is positioned to contact the portion of the lumen in the treatment member that possesses the inner diameter smaller than the outer diameter of the enlarged diameter portion to limit axial movement of the inner tubular member relative to the treatment member.

According to another aspect, a medical device for treating a stenotic region in a body lumen in a living body comprises a treatment member, a rotatable drive shaft, and a tubular member. The treatment member is positionable in the body lumen in the living body adjacent the stenotic region and possesses an outer surface for grinding the stenotic region in the body lumen in the living body. The rotatable drive shaft is connectable to a motor so that operation of the motor results in rotation of the drive shaft and the treatment member to grind the stenotic region in the body lumen in the living body, and the tubular member includes an axially extending lumen that extends throughout an axial extent of the tubular member so that the lumen opens to opposite ends of the tubular member. A distal part of the tubular member is positioned in the lumen of the treatment member so that the distal part of the tubular member and the treatment member axially overlap one another. The treatment member and the tubular member are relatively rotatable, the tubular member includes a portion possessing an outer diameter, and a part of the lumen in the treatment member possesses an inner diameter smaller than the outer diameter of the portion of the tubular member to limit relative axial movement between the tubular member and the treatment member by virtue of contact between the portion of the tubular member and the part of the lumen in the treatment member.

According to a further aspect, a medical device for treating a stenotic region in a living body comprises a drive shaft connectable to a motor so that operation of the motor results in rotation of the drive shaft, a treatment member connected to a distal portion of the drive shaft and including an outer surface and an inner edge, and an inner tubular member positioned in the treatment member. The inner tubular member includes an enlarged outer diameter portion and an axially extending lumen that extends throughout an axial extent of the inner tubular member so that the lumen opens to a distal-most end of the inner tubular member and to a proximal-most end of the inner tubular member to permit positioning a guidewire in the lumen. The treatment member is rotatable relative to the inner tubular member, and the inner tubular member is limited in axial movement in a distal direction relative to the treatment member by virtue of the enlarged outer diameter portion of the inner tubular member engaging the inner edge of the treatment member.

BRIEF DESCRIPTION OF DRAWING FIGURES

FIG. 7A is a cross-sectional view of the treatment member and outer tubular member taken along the section plane identified as 7A in FIG. 5, and FIG. 7B is a similar cross-sectional view illustrating shearing action following relative rotation between the treatment member and the outer tubular member.

Figure 6:
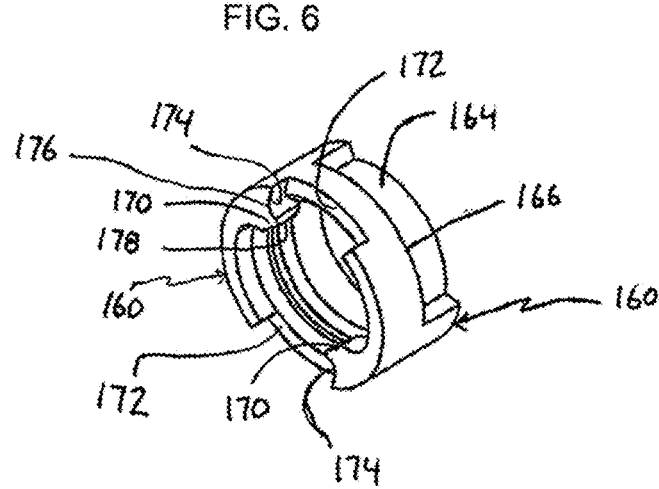
FIG. 6 is a perspective view of the outer tubular member that is mounted on the treatment member.
Figure 10A:
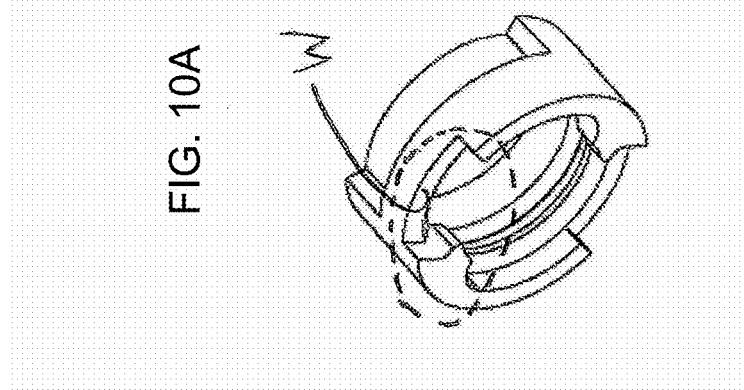
Figure 10J:
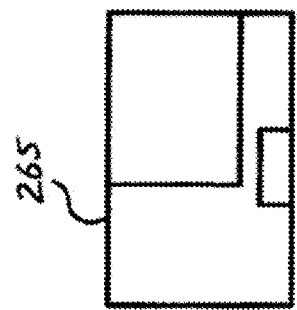
Figure 10K:
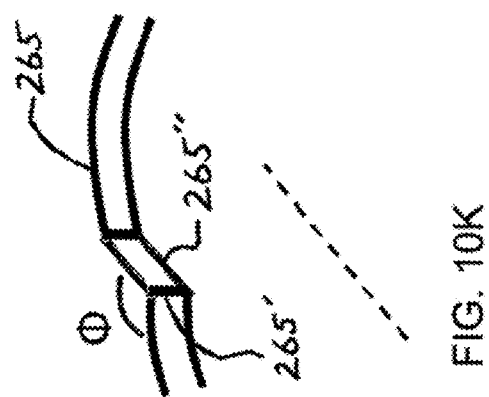
Figure 10L:
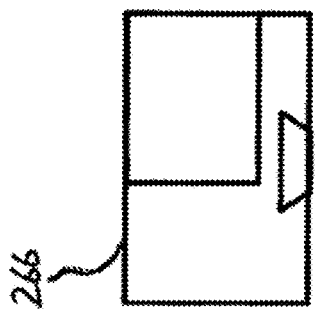
Figure 10M:
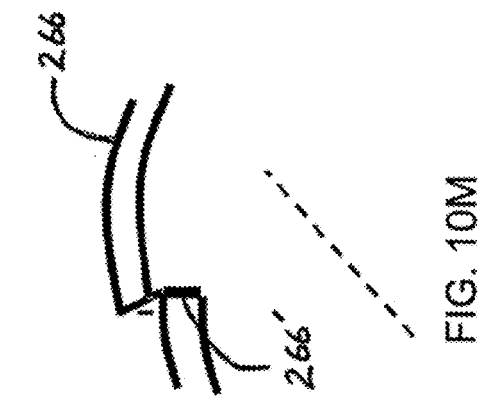
Figure 10N:
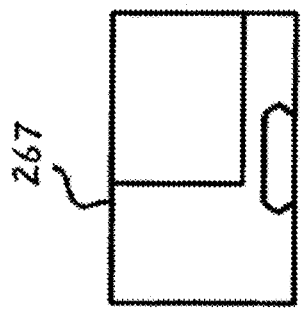
Figure 10O:
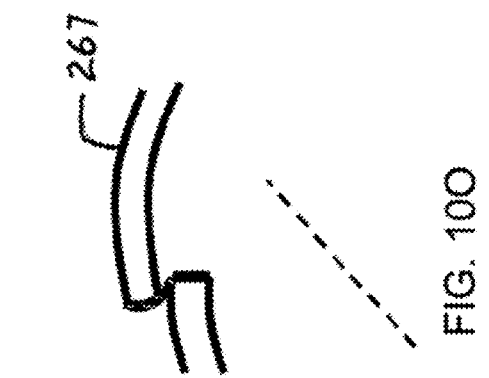

FIG. 10A is a perspective view of the outer tubular member shown in FIG. 6 identifying, in dotted outline, the location at which the top and perspective views shown in FIGS. 10B-10O are taken, in which FIGS. 10B and 10C are top and perspective views respectively of one alternative embodiment of the shearing edge of the outer tubular member that interacts with the shearing edge on the treatment member to create shearing action that acts on debris resulting from grinding substance in the body lumen, in which FIGS. 10D and 10E are top and perspective views respectively of another embodiment of the shearing edge of the outer tubular member, FIGS. 10F and 10G are top and perspective views respectively of another embodiment of the shearing edge of the outer tubular member, FIGS. 10H and 10I are top and perspective views respectively of a further embodiment of the shearing edge of the outer tubular member, FIGS. 10J and 10K are top and perspective views respectively of an embodiment in which the outer tubular member is devoid of the inwardly directed protrusion but still generates a shearing force, FIGS. 10L and 10M are top and perspective views respectively of another embodiment in which the outer tubular member is devoid of the inwardly directed protrusion but still generates a shearing force, and FIGS. 10N and 10O are top and perspective views respectively of a further embodiment in which the outer tubular member is devoid of the inwardly directed protrusion but still generates a shearing force.

Figure 4:
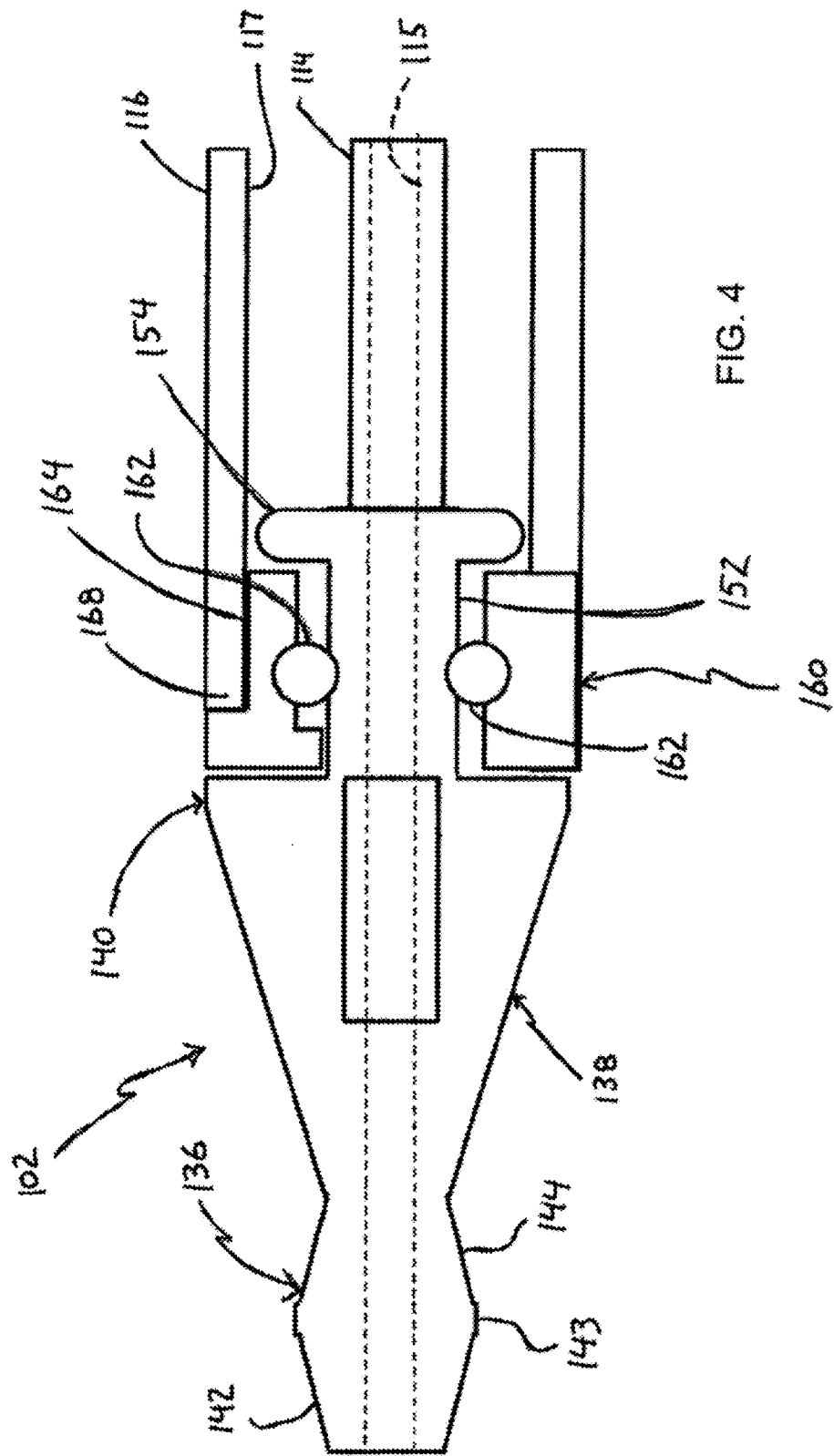
FIG. 4 is a cross-sectional view of the treatment member illustrated in FIG. 3.
Figure 5:
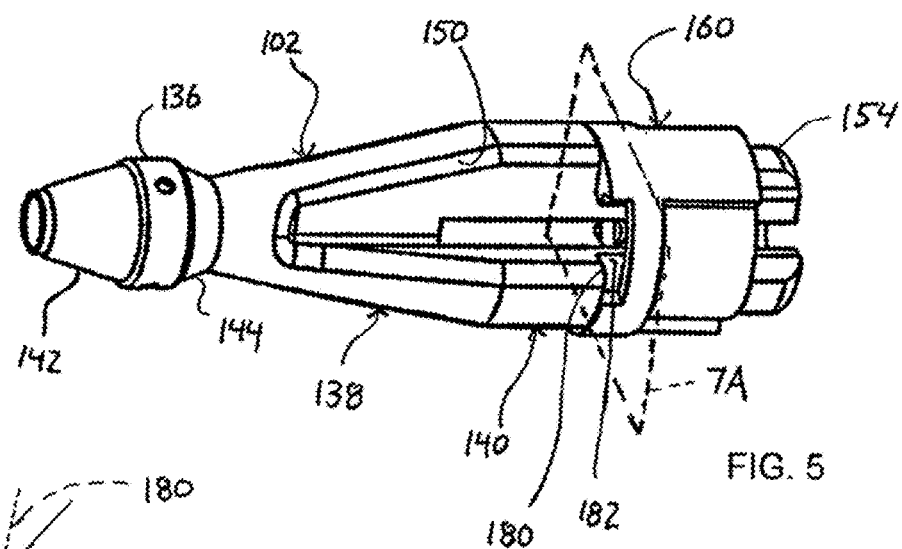
FIG. 5 is another perspective view of the treatment member forming part of the medical device shown in FIG. 1.
Figure 11:
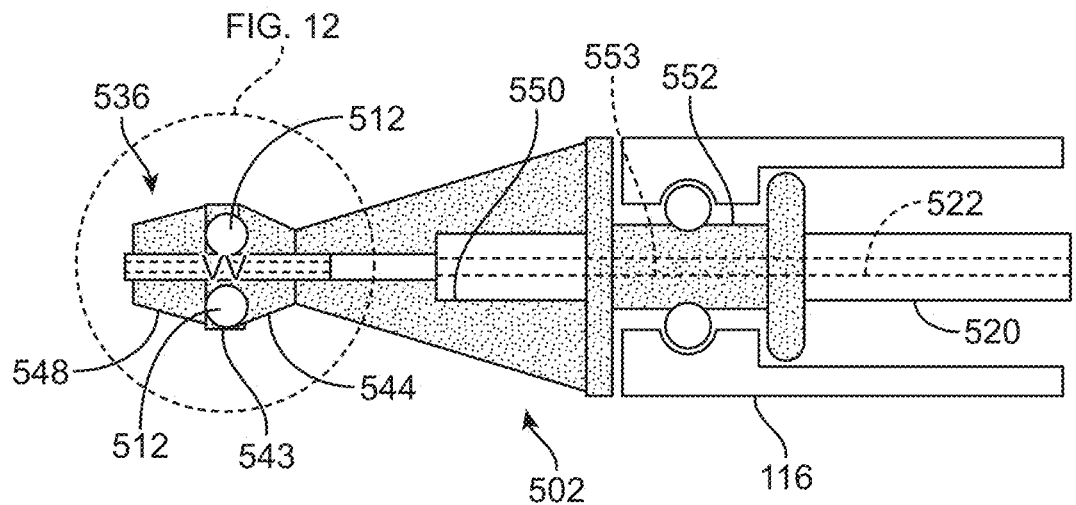

FIG. 11 is a cross-sectional view of the treatment member similar to that illustrated in FIG. 4, but depicting a different aspect of the medical device involving a bearing arrangement.

Figure 12:
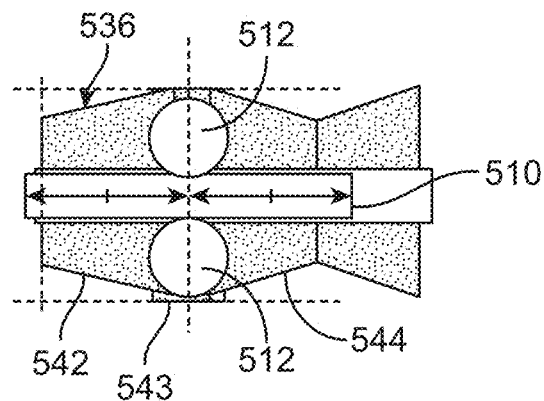

FIG. 12 is an enlarged cross-sectional view of the treatment member shown in FIG. 11 illustrating aspects of the inner tubular member constituting a bearing arrangement.

Figure 13:
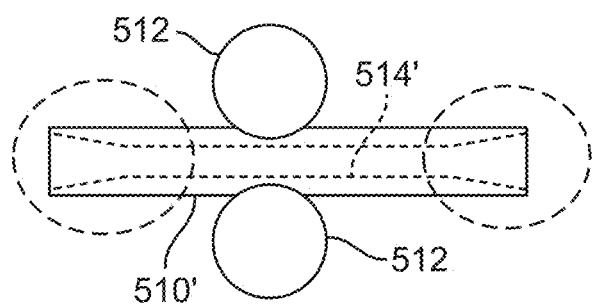

FIG. 13 is a cross-sectional view of a variation on the inner tubular member constituting the bearing arrangement shown in FIG. 12.

Figure 14A:
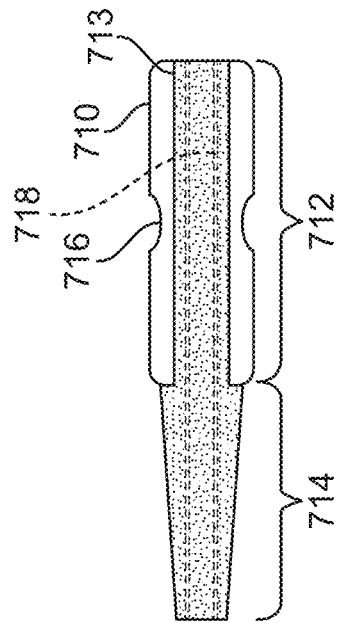
Figure 14B:
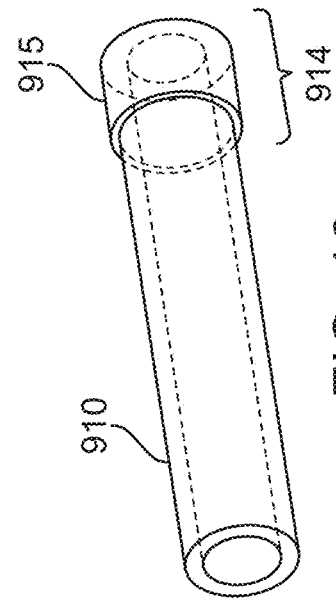

FIGS. 14A and 14B are side views of alternative embodiments of the inner tubular member constituting the bearing arrangement.

Figure 15:
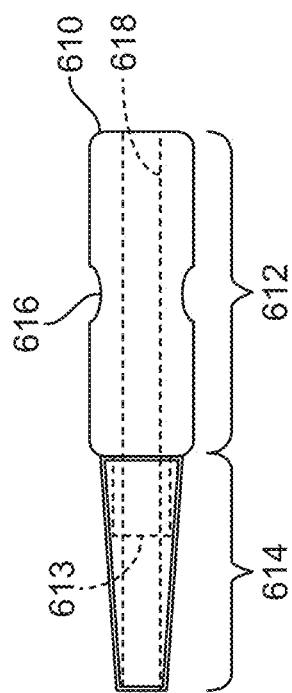

FIG. 15 is a perspective view of another embodiment of the inner tubular member constituting the bearing arrangement.

Figure 16:
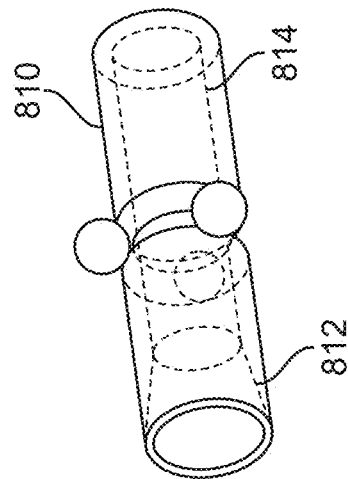

FIG. 16 is a perspective view of another embodiment of the inner tubular member constituting the bearing arrangement.

Figure 17A:
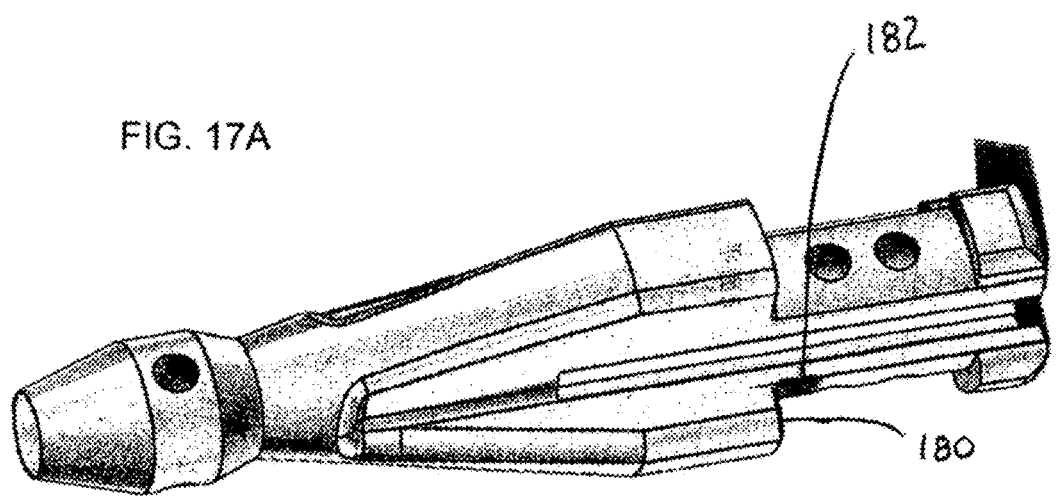
Figure 17B:
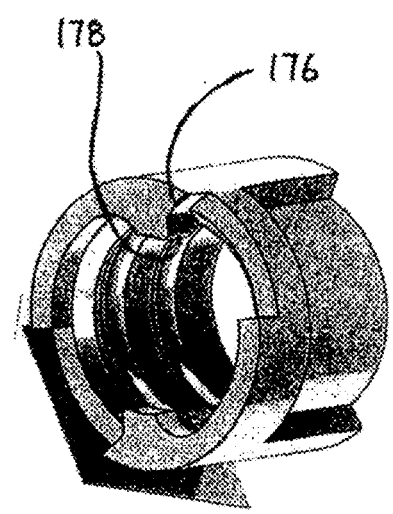

FIGS. 17A and 17B are perspective views of the treatment member and the outer tubular member respectively identifying the shearing edges or shearing portions.

FIGS. 18A-18D are perspective views of embodiments of the inner tubular member constituting the bearing arrangement.

Figure 19:
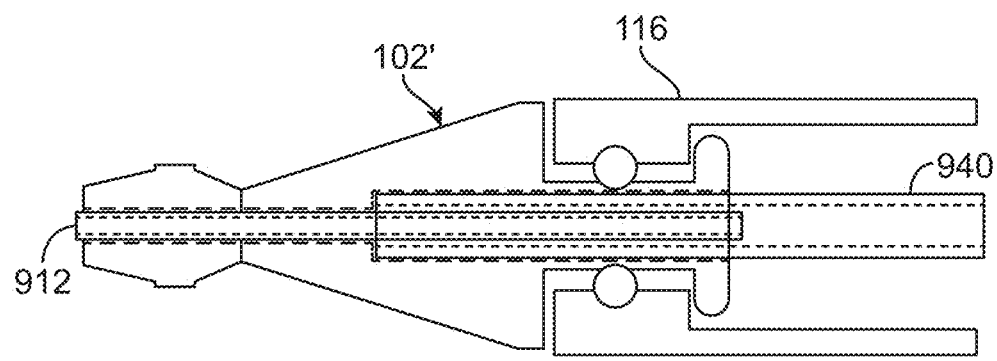

FIG. 19 is a cross-sectional view of another embodiment of the treatment member with a bearing arrangement.

DETAILED DESCRIPTION

Figure 1:
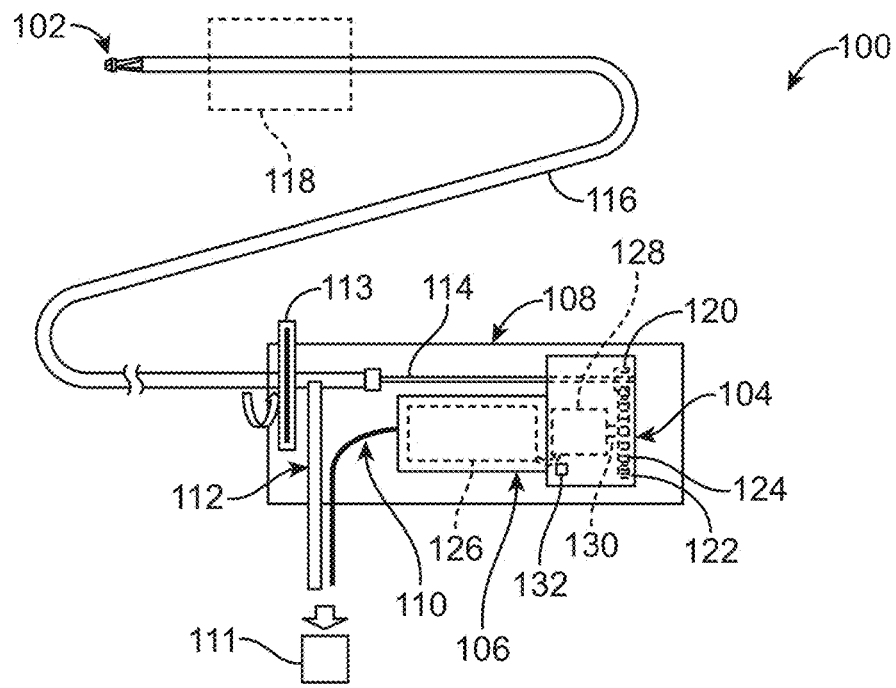
FIG. 1 is a schematic view of the medical device according to one embodiment.

Set forth below with reference to the accompanying drawings is a detailed description of embodiments of a medical device and method for removing substance from a body lumen in a living body representing examples of the medical device and method disclosed here FIG. 1 schematically illustrates one embodiment of the medical device representing an example of the inventive medical device disclosed here. This disclosed medical device is configured to grind a substance in a body lumen such as arteriosclerosis in a blood vessel. The terms "grind" and "grinding" as used here are not limited to any particular operation or manner of acting on the substance, and include operations such as grinding, scraping, abrading, ablating, macerating and otherwise breaking down desired substance or material into particles or other smaller units of material to facilitate removal from the living body (e.g., blood vessel).

Figure 2A:
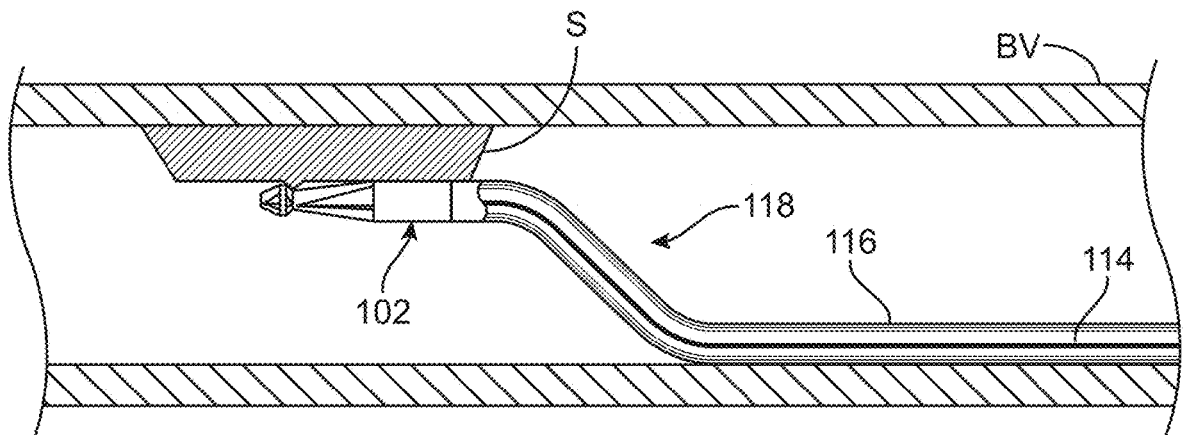
FIGS. 2A and 2B are cross-sectional views of the distal portion of the medical device, including the treatment member, positioned in a blood vessel to grind-away a substance in the blood vessel.
Figure 2B:
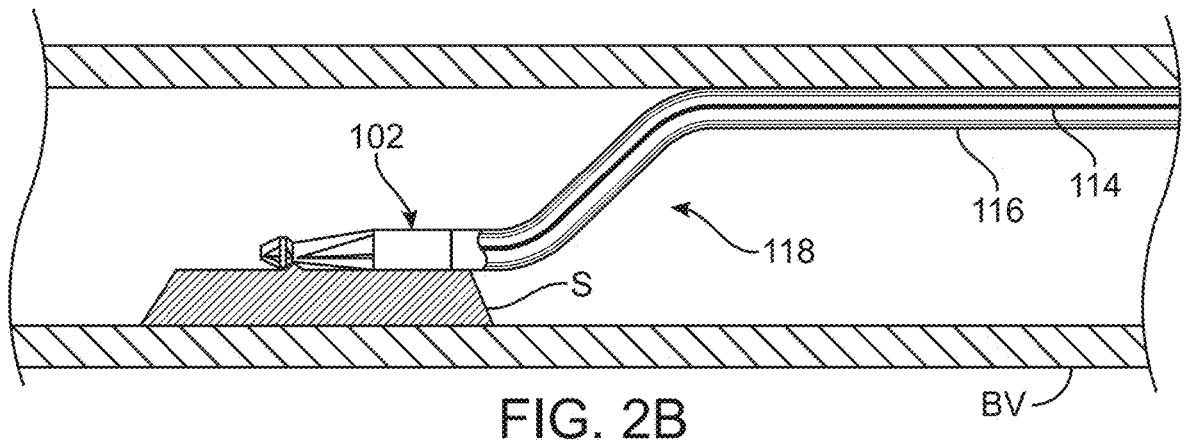

The medical device 100 shown in FIG. 1 can be used to grind a stenosis S such as shown in FIGS. 2A, 2B from a blood vessel BV, which stenosis can be constituted by a thrombus, calcified lesion, etc. Referring initially to FIG. 1, the medical device 100 may include a treatment member 102 and an operation unit 104 configured to transmit a rotation driving force to the treatment member 102 to rotate the treatment member 102. The operation unit 104 may be housed in a handle 108.

The operation unit 104 includes a motor 128 that produces a rotational output force. The operation unit 104 also includes a drive mechanism section 122 for transmitting or applying the rotational output shaft of the motor 128 to the drive shaft 114. The drive mechanism section 122 includes a drive gear 124 and a driven gear 120 that mesh with one another so that rotation of the drive gear 124 results in rotation of the driven gear 120. The motor 128 serves as a driving source and includes a rotatable motor shaft 130 to which the drive gear 124 is fixed so that the motor shaft 130 and the drive gear 124 rotate together as a unit. Operation of the motor 128 causes rotation of the motor shaft 130 which in turn results in rotation of the drive gear 124. The proximal end of the drive shaft 114 may be fixed to the driven gear 120 so that the drive shaft 114 and the driven gear 120 rotate together as a unit. Thus, the operation of the motor 128 and the rotation of the motor shaft 130 is transmitted to the treatment member 102 by way of the drive gear 124, the driven gear 120 and the drive shaft 114. A power supply section 106 that includes a battery 126 may be provided in the handle 108 and connected to the motor 128 to supply power to the motor 128. A power cable 110 may be connected to the battery 126 to supply power. FIG. 1 also shows that the medical device 100 may be provided with an aspiration tube 112 to remove (i.e., draw-away or suck-away) debris resulting from the grinding of the substance S.

The drive shaft 114 may be comprised of a tubular drive shaft that is hollow so that a central lumen extends throughout the entire axial extent of the drive shaft 114. The drive shaft 114 may preferably be flexible, but also well suited to transmitting the rotational output of the motor unit from the proximal end of the drive shaft 114 to the distal end of the drive shaft 114 at which the treatment member 102 is located. The drive shaft 114 may be any desired construction. For example, the drive shaft 114 may be constituted by a single or multi-layer structure. As an example, the drive shaft 114 may be configured as a single or multi-layered coiled wire or tube made from, for example, SUS, NiTi as metal, or a polyolefin such as polyethylene or polypropylene, polyamides, polyesters such as polyethylene terephthalate, fluorine series such as PTFE Polymer, PEEK, polyimide, or combinations thereof. The tubular drive shaft can also be provided with reinforcement. The size of the drive shaft may be appropriately selected. Examples of an appropriate size include an inner diameter of 0.40 mm-1.40 mm and an outer diameter of 0.6 mm-1.6 mm.

The drive shaft 114 is preferably a tubular drive shaft as mentioned above so that the drive shaft includes a lumen defining a guidewire-receiving passage. The guidewire passes through the lumen in the drive shaft and allows the drive shaft 114 together with the treatment member 102 to be navigated through the living body (e.g., the lumen of a blood vessel) to position the treatment member 102 at the desired place adjacent substance to be ground.

The drive shaft 114 may be housed in a tubular outer sheath 116. The outer sheath 116 may be a tubular body that accommodates the drive shaft 114 so that the drive shaft 114 is rotatable and axially movable relative to the outer sheath 116 and in the outer sheath 116. The material forming the outer sheath 116 is not limited to a particular material. By way of example, the outer sheath 116 may be made of SUS, NiTi as metal, or polyethylene, polypropylene, polyolefin such as polyethylene terephthalate, polyester such as polyamide terephthalate, fluorine-based polymers such as PTFE, PEEK, polyimide and the like or combinations of such materials.

The operation of the motor 128 can be controlled by way of a switch 132. Operating or turning on the switch 132 causes the motor 128 to operate and rotate the motor shaft 130. As a result, the drive gear 124 rotates and in turn rotates the driven gear 120 which meshes with the drive gear 124. The rotation of the driven gear 120 results in rotation of the drive shaft 114 and ultimately rotation of the treatment member 102. The medical device 100 also includes a rotation mechanism 113, schematically illustrated in FIG. 1, that is operationally connected to the outer sheath 116 to rotate the outer sheath as generally indicated by the arrow in FIG. 1.

FIGS. 2A and 2B illustrate that a bending section 118 may be provided in the tubular outer sheath 116 and the drive shaft 114. This bending section 118 may be provided at an intermediate point along the length of the drive shaft 114 and the outer sheath 116. In this bending section 118, the outer sheath 116 and the drive shaft 14 are bent such as illustrated in FIGS. 2A, 2B. This allows the treatment unit 102 to be manipulated in a way that allows grinding of the stenosis S located in a blood vessel BV. That is, as the drive shaft 114 is rotated by operation of the motor 128 and as the outer sheath 116 is rotated by operation of the rotation mechanism 113, the treatment member 102 traces a movement path that is circular or annular, while at the same time the treatment member 102 rotates about its central axis. FIGS. 2A and 2B also illustrate that, during operation of the medical device while the treatment member 102 is positioned in the living body (blood vessel) and is being rotated, the distal end portion of the treatment member 102 is positioned distally beyond the distal-most end of the outer sheath 116.

Figure 3:
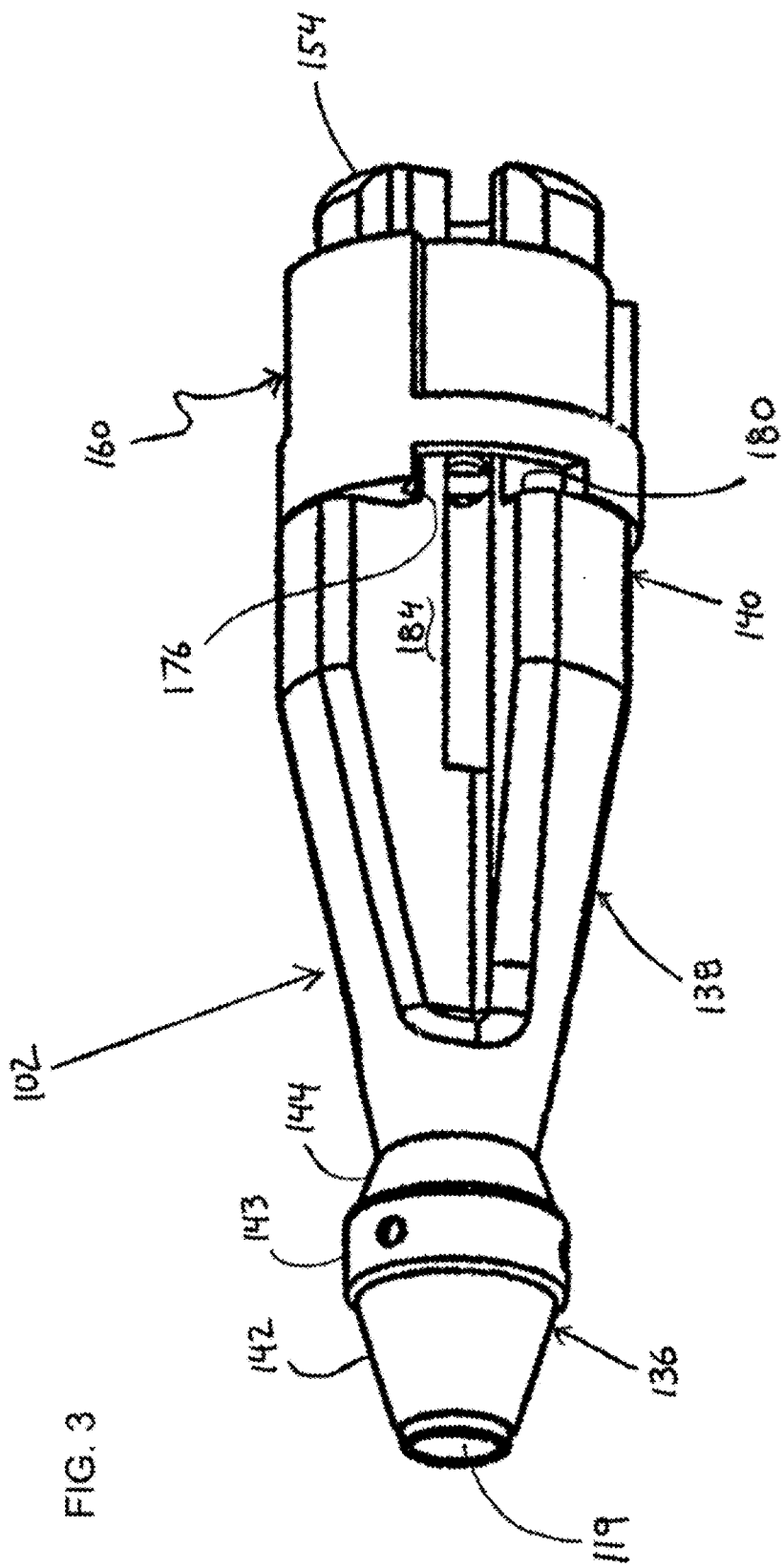
FIG. 3 is a perspective view of one version of the treatment member forming part of the medical device shown in FIG. 1.

FIGS. 3 and 4 illustrate additional details associated with the treatment member 102 that is connected to the distal end of the drive shaft 114. FIGS. 3 and 4 illustrate the centrally located guidewire lumen 115 that may be centrally provided in the drive shaft 114 for receiving a guidewire as discussed above. As mentioned above, during operation of the medical device, the distal end portion of the treatment member 102 is positioned distally beyond the distal-most end of the outer sheath 116. FIGS. 3 and 4 show that the treatment member 102 that extends distally beyond the distal-most end of the tubular outer sheath 116 and is thus exposed (i.e., the treatment member 102 not covered by the outer sheath 116). The treatment member 102 that is exposed distally beyond the distal end of the outer sheath 116 during operation may be comprised of a distal-most end portion 136, an intermediate portion 138 and a proximal end portion 140. The intermediate portion 138 is positioned axially between the distal-most end portion 136 and the proximal end portion 140. The distal-most end portion 136, the intermediate portion 138 and the proximal end portion 140 may preferably be configured to facilitate grinding of the substance in the body lumen (e.g., stenosis S in a blood vessel BV). One way of accomplishing this result is to provide the distal-most end portion 136, the intermediate portion 138 and the proximal end portion 140 of the treatment member 102 with a coating that helps facilitate the grinding of the substance in the body lumen. An example of the coating is a diamond grind coating. Diamond grind coating refers to a coating comprised of diamond grit, involving relatively small pieces of diamond (e.g., ~30 um in diameter), and metal electroplating (Ni, Co, Cr, etc.). An example of this type of coating is the coating used in electroplated diamond tools produced by PFERD.

The distal-most end portion 136 of the treatment member 102 is comprised of a distally tapering portion 142 and a proximally tapering portion 144. The proximally tapering portion 144 is positioned proximal of the distally tapering portion 142. The distally tapering portion 142 constantly tapers in a narrowing manner towards the distal-most end of the treatment member 102 while the proximally tapering portion 144 constantly tapers in a narrowing manner towards the proximal-most end of the treatment member 102. The distal-most end portion 136 of the treatment member 102 may also comprise a constant outer diameter intermediate portion 143 positioned between the distally tapering portion 142 and the proximally tapering portion 144. In the illustrated embodiment, the coating that helps facilitate the grinding of the substance in the body lumen is not provided on the constant outer diameter intermediate portion 143. Of course, the coating applied to the outer surface of the remainder of the treatment member 102 may also be provided on the outer surface of the constant outer diameter intermediate portion 143. The intermediate portion 143 may be in the form of a cover ring for a front ball bearing that helps facilitate rotation.

The intermediate portion 138 may be a tapering portion as illustrated in FIGS. 3 and 4 in which the intermediate portion tapers in a constant manner along its entire extent from the proximal-most end of the intermediate portion 138 to the distal-most end of the intermediate portion 138. The intermediate portion 138 tapers towards the distal-most end of the treatment member 102 so that the outer diameter of the intermediate portion 138 gradually narrows in the distal direction.

The proximal end portion 140 may possess a constant outer diameter along its entire axial extent as shown in FIGS. 3 and 4.

The treatment member 102 is also provided with at least one window or through opening 150 that communicates with the hollow interior or lumen inside the treatment member 102. The treatment member 102 may include a plurality of circumferentially spaced-apart windows or through openings 150. For example, as illustrated in FIGS. 7A and 7B, the treatment member 102 may be provided with three windows or through openings 150 that are circumferentially spaced apart at equal angular intervals. Of course, a different number of windows or through openings may be provided, and they may be arranged at different relative positions than that shown in FIGS. 7A and 7B.

As mentioned above, each of the windows or through openings 150 opens into and communicates with the hollow interior or lumen (gateway lumen) in the treatment member 102. The lumen or hollow interior of the treatment member 102 is in communication with the lumen 117 in the outer sheath 116 as shown in FIG. 4. The aspiration tube 112 shown in FIG. 1 is connected to or fluidly communicates with the lumen 117 in the outer sheath 116. The aspiration tube 112 is connected to an aspiration source or suction device 111 schematically illustrated in FIG. 1.

During operation of the medical device 100, the treatment member 102 is rotated by operation of the motor 128 to grind the substance S in the body lumen BV (e.g., stenosis in the blood vessel). While the treatment member 102 is grinding the substance in the body lumen, the suction source 111 is operated to draw debris resulting from the grinding operation through the windows or through openings 150 in the treatment member 102, into the lumen or hollow interior in the treatment member 102, and into the lumen 117 in the outer sheath 116. The debris is then drawn out of or removed from the body lumen by way of the suction device 111.

As illustrated in FIG. 4, the proximal end portion of the treatment member 102 includes a reduced outer diameter portion defining a shaft portion 152 of the treatment member 102. This reduced-outer diameter shaft portion 152 of the treatment member 102 represents a seating region for receiving an outer tubular member 160 representing a shaft bearing or bush member. A lumen extends throughout the entire axial extent of the outer tubular member 160 (i.e., passes through the outer tubular member 160), and the reduced-outer diameter shaft portion 152 of the treatment member is positioned in the lumen that extends throughout the entire axial extent of the outer tubular member 160. The outer tubular member 160 is thus mounted on the treatment member 102. The tubular member 160 is rotatable relative to the treatment member 102. That is, as described above, the treatment member 102 is rotatably driven by way of the drive shaft 114, and the treatment member 102 rotates relative to the tubular member 160.

An axially extending lumen extends throughout the entire length of the reduced-outer diameter shaft portion 152 (i.e., passes through the reduced-outer diameter shaft portion 152). This lumen in the reduced-outer diameter shaft portion 152 communicates with and is coaxial with the lumen 115 in the drive shaft 114. The lumen in the reduced-outer diameter shaft portion 152 is also coaxial with the open end 119 at the distal-most end of the treatment member 102 shown in FIG. 3 and opens into and communicates with the lumen in the treatment member 102.

A bearing may be positioned between the outer surface of the reduced outer diameter shaft portion 152 and the inner surface of the outer tubular member 160 to facilitate the relative rotation between the reduced outer diameter shaft portion 152 and the outer tubular member 160. The outer tubular member 160 may thus be mounted on the treatment member 102, with a bearing between the outer tubular member 160 and the treatment member 102. The bearing may be of any desired configuration, including a plurality of roller bearings 162 as shown in FIG. 4. The roller bearings 162 help facilitate relative rotation between the treatment member 102 and the outer tubular member 160.

As illustrated in FIG. 4, the outer peripheral surface of the outer tubular member 160 may be recessed to define a radially inwardly recessed portion defining a recess 164. The recess 164 is of limited circumferential extent (i.e., the recess 164 does not extend around the entire circumferential extent of the outer tubular member 160) so that the recess 164 possesses a circumferential extent less than 360°, preferably less than 180°. The recess 164 extends from the proximal-most end of the outer tubular member 160 towards the distal end of the outer tubular member 160. The recess 164 thus opens to the proximal-most end of the outer tubular member 160 and extends less than the entire axial extend of the outer tubular member 160 so that the distal-most end of the recess 164 is defined by a wall 166. FIG. 4 illustrates that the recess 164 in the outer surface of the outer tubular member 160 receives a distally extending projection at the distal end portion of the outer sheath 116. The engagement between the distally extending projection 168 of the outer sheath 116 and the recess 166 in the outer tubular member 160 rotationally fixes the outer sheath 116 and the outer tubular member 160 so that the outer sheath 116 and the outer tubular member 160 do not rotate relative to each other. Thus, when the treatment member 102 is rotated by operation of the motor 128, the treatment member 102 rotates relative to both the outer sheath 116 and the outer tubular member 160.

The outer tubular member 160 may also include at least one radially inwardly directed protrusion 170. In the illustrated embodiment of the outer tubular member shown in FIG. 6, the outer tubular member 160 includes two protrusions 170, each of which is directed radially inwardly toward the lumen that extends axially throughout the outer tubular member 160. The two protrusions 170 may be positioned diametrically opposite one another. Each of the protrusions 170 is of limited circumferential extent, meaning that each of the protrusions has a circumferential extent less than 360° as seen from the axial end of the outer tubular member 160. Each of the protrusions 170 may possess a circumferential extent less than 180°, more preferably less than 90°. Each of the protrusions is of a limited circumferential extent so that the protrusion 170 possesses two circumferentially spaced apart side surfaces that each extend from the outer peripheral surface of the outer tubular member 160 toward the lumen of the outer tubular member 160. The protrusion may be formed in part of the distal end of the outer tubular member.

Figure 8:
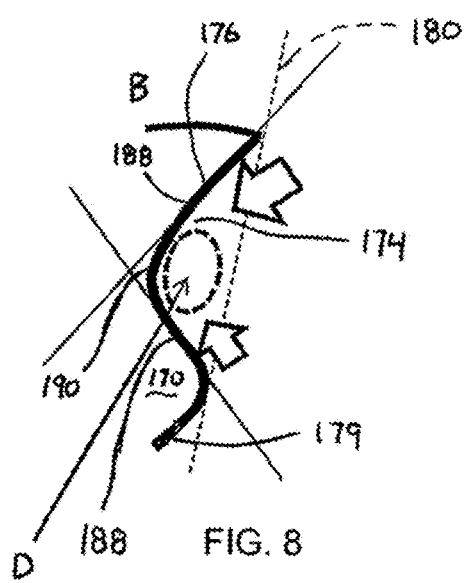
FIG. 8 is an enlarged view of a shearing edge of the outer tubular member that interacts with a shearing edge on the treatment member to create shearing action that acts on debris resulting from grinding substance in a body lumen of a living body.

The outer tubular member 160 may also include a recess 172 positioned on one circumferential side of each protrusion 170. That is, as illustrated in FIG. 6, a recess 172 is positioned in front of each projection 172 in the clockwise direction. The recess 172 is thus bordered on one circumferential side by the side surface of the protrusion 170. Each recess 172 may be an axially directed recess, meaning that each recess 172 is recessed from the distal-most axial end surface (axial end surface at the left in FIG. 6) of the outer tubular member 160 in the axial direction toward the proximal-most axial end (axial end at the right in FIG. 6) of the outer tubular member 160. This thus creates a trough or axially indented region along one side of each protrusion 170. Each of these troughs 174 is configured to receive debris D resulting from grinding the substance S in the body lumen BV (arteriosclerosis in a blood vessel). An example of this debris received in the trough 174 is generally illustrated in FIG. 8.

Each of the protrusions 170 is configured to define two shearing portions, each of which interacts with a respective shearing portion on the treatment member 102 to impart a shearing force to the debris D. This shearing force applied to the debris D helps break-up the debris or reduce the size of the debris. As shown in FIG. 6, for example, a first one of the shearing portions on the outer tubular member 160 includes the shearing edge 176 on the edge of the protrusion 170. This first shearing portion 176 defined by the edge of the protrusion 170 is a radially extending shearing edge of the outer tubular member 160, meaning it extends in a direction from the outer surface of the outer tubular member 160 to the inner surface of the outer tubular member 160.

The second shearing portion on the outer tubular member 160 is defined by the shearing edge 178 on the inner periphery of the projection 170. This second shearing portion 178 defined by the edge on the inner periphery of the projection 170 is an axially extending shearing edge of the outer tubular member 160, meaning it extends in the axial direction parallel to the central axis of the outer tubular member 160. FIG. 17B identifies the first shearing portion 176 on the outer tubular member 160 and the second shearing portion 178 on the outer tubular member 160.

The first shearing portion (shearing edge) on the tubular member 160 interacts with a first shearing portion or shearing edge 180 on the treatment member 102. The first shearing portion 180 on the treatment member 102 is defined by the radially extending edge at the distal axial end of the reduced outer diameter portion 152 adjoining the window 150. The first shearing portion or shearing edge 176 on the tubular member 160 and the first shearing portion or shearing edge 180 on the treatment member 102 radially overlap one another during the relative rotation between the treatment member 102 and the outer tubular member 160, meaning they have similar radial extents. During rotation of the treatment member 102 relative to the tubular member 160, debris D positioned in the trough 174 of the tubular member 160 is subjected to a shearing action between the first shearing portion or shearing edge 176 on the tubular member 160 and the first shearing portion or shearing edge 180 on the treatment member 102.

The second shearing portion (shearing edge) 178 on the tubular member 160 interacts with a second shearing portion or shearing edge 182 on the treatment member 102. The second shearing portion 182 on the treatment member 102 is defined by the axially extending edge at the reduced outer diameter portion 152 adjoining the window 150. The second shearing portion or shearing edge 178 on the tubular member 160 and the second shearing portion or shearing edge 182 on the treatment member 102 axially overlap one another during the relative rotation between the treatment member 102 and the outer tubular member 160, meaning they have similar axial extents. During rotation of the treatment member 102 relative to the outer tubular member 160, debris D in the trough 174 of the outer tubular member 160 will be subjected to a shearing action between the second shearing portion 178 on the tubular member 160 and the second shearing portion 182 on the treatment member 102. FIG. 17A identifies the first shearing portion 180 on the treatment member 102 and the second shearing portion 182 on the treatment member 102.

Thus, as the treatment member 102 positioned in the body lumen rotates relative to the outer tubular member 160 during grinding of the substance S in the body lumen BV, debris D in the trough 174 of the outer tubular member 160 will be subjected to either or both a shearing force between the first shearing portion or shearing edge 176 on the tubular member 160 and the first shearing portion or shearing edge 180 on the treatment member 102, and the shearing force between the second shearing portion or shearing edge 178 on the tubular member 160 and the second shearing portion or shearing edge 182 on the treatment member 102. This shearing force(s) will breakup or reduce the size of the debris D. As a result, the size of the debris entering the lumen 184 (schematically shown by the axially directed dotted line arrow in FIG. 3) will be reduced in size and will be less susceptible to causing blockage of the lumen 184. The rotation speed of the treatment member may range from 5,000 rpm to 200,000 rpm, more preferably 10,000 rpm to 120,000 rpm. The rotational speed of the outer sheath can be 5 rpm to 5,000 rpm. The rotational direction of the treatment member may be the same as the rotational direction of the outer sheath. The rotational direction of the treatment member may be the opposite of the rotational direction of the outer sheath. As described above, the rotation of the outer sheath can be carried out by way of the rotation mechanism 113 schematically shown in FIG. 1.

As illustrated in FIG. 8, the first shearing portion or shearing edge 176 of the outer tubular member 160 is generally defined by two linear or straight segments (edge portions) 188 that intersect or meet at a curved segment (edge portion) 190 so that the first shearing portion 176 exhibits the configuration or shape shown in FIG. 8. During the rotation of the treatment member 102 relative to the outer tubular member 160, forces are applied to the debris D as generally indicated by the arrows in FIG. 8. The arrows show that the force at the outer diameter is greater than the force at the inner diameter so that the debris resulting from grinding the substance is forced into the radially inner side. This may be helpful from the standpoint of aspirating debris.

In the embodiment of the shearing mechanism illustrated in FIG. 8, the shape of the inner surface or inner periphery of the protrusion 170 matches or is the same as the shape of the outer periphery or outer surface of the reduced outer diameter portion 152 of the treatment member 102. Thus, the shape of the second shearing portion or shearing edge 178 on the tubular member 160 matches or is the same as the shape of the second shearing portion or shearing edge 182 on the treatment member 102.

Figure 9B:
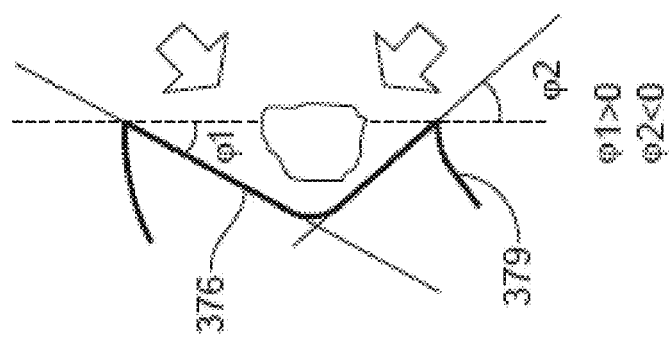
FIGS. 9A and 9B are enlarged views of alternative embodiments of the shearing edge of the outer tubular member that interacts with the shearing edge on the treatment member to create shearing action that acts on debris resulting from grinding substance in the body lumen.
Figure 9A:
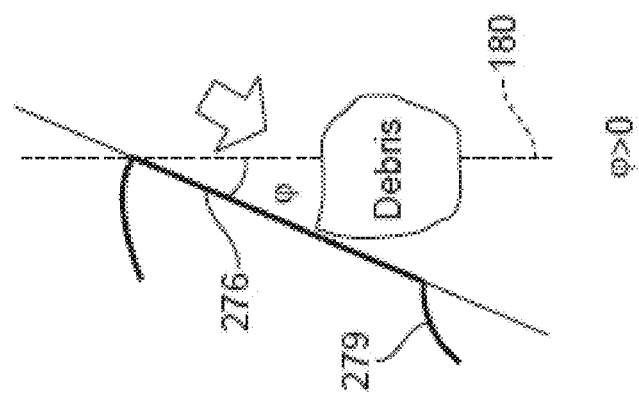

FIG. 9A illustrates a modified version of the first shearing portion or shearing edge on the tubular section 160 and the second shearing portion or shearing edge on the tubular member 160. In this embodiment, the first shearing portion or shearing edge 276 on the outer tubular member is in the form of a straight or linear shearing portion (linear shearing edge) that is straight or linear along its entire extent. During rotation of the treatment member 102 relative to the outer tubular member 160, the debris resulting from the grinding of the substance S in the body lumen BV (arteriosclerosis in a blood vessel) is subjected to a force indicated by the arrow 9A to urge the debris D towards the shearing region defined by the second shearing portion or shearing edge of the outer tubular member 160 and the second shearing portion 182 of the treatment member 102. The second shearing portion or shearing edge of the outer tubular member is an axially extending shearing edge similar to the second shearing portion or shearing edge 178 shown in FIG. 6. The first shearing portion or shearing edge 276 on the outer tubular member forms an angle φ with the first shearing portion or shearing edge 180 of the outer tubular member 160 when the outer point of the first shearing portion or shearing edge 276 intersects the first shearing portion or shearing edge 180 of the outer tubular member 160. The angle φ may be greater than 0°. The relationship φ1>0° may be beneficial in terms of helping to push debris inwardly, a result that may be helpful for aspiration purposes.

The configuration of the inwardly directed protrusion shown in FIG. 9A is also slightly different from the configuration of the inwardly directed protrusion 170 shown in FIG. 8. In the embodiment shown in FIG. 9A, the shape of the portion 279 of the inwardly directed protrusion of the outer tubular member 160 does not match the shape of the outer periphery of the reduced outer diameter portion of the treatment member 102.

FIG. 9B illustrates a further embodiment of the configuration of the shearing mechanism on the outer tubular member. In the embodiment shown in FIG. 9B, the shearing mechanism includes a first shearing portion or shearing edge 376 that is the same as that shown in FIG. 8 and described above, and a second shearing portion or shearing edge that is also similar to the second shearing portion or shearing edge 178 shown in FIG. 8. In the FIG. 9B embodiment, the shape of the portion 379 of the inwardly directed protrusion of the outer tubular member is like that shown in FIG. 9A in that the shape of the portion 379 does not match the shape of the outer periphery of the reduced outer diameter portion of the treatment member 102. This configuration of the shearing mechanism produces an angle φ1 greater than 0° and an angle φ2 less than 0°. The relationships φ1>0 and φ2<0 shown in FIG. 9B may be beneficial in terms of catching debris at the center of the curved structure 376 (176) to impart a strong force to debris to make them tiny pieces.

FIGS. 10B-10O illustrate further embodiments of the configuration of the shearing portions or shearing edges on the outer tubular member. The dotted outline in FIG. 10A identifies the location at which the top and perspective views in FIGS. 10B-10O are taken. The embodiment of the outer tubular member 261 shown in FIGS. 10B and 10C is devoid of the window or recess on the outer axial surface of the tubular member (i.e., the window W shown in FIG. 10A, which is similar to the axially directed recess 172 shown in FIG. 6, is not present in the embodiment shown in FIGS. 10B and 10C), and includes the first shearing edge 261' and the second shearing edge 261", with the second shearing edge 261" being parallel to the center axis (shown as the dotted line in FIG. 10C) of the outer tubular member. In the embodiment of the outer tubular member 262 shown in FIGS. 10D and 10E, the window or axially extending recess on the outer axial surface of the tubular member is configured so that a 90° angle (φ=90°) exists between the wall of the window and the outer axial surface, and includes the first shearing edge 262' and the second shearing edge 262", with the second shearing edge 262" being parallel to the center axis of the outer tubular member. As shown in FIG. 10D, the window or axially extending recess W on the outer axial surface of the tubular member is rectangular-shaped as seen from the top. In the embodiment of the outer tubular member 263 shown in FIGS. 10F and 10G, the window or axially extending recess on the outer axial surface of the tubular member is configured so that the angle φ between the wall of the window and the outer axial surface is less than 90° (φ<90°), and includes the first shearing edge 263' and the second shearing edge 263", with the second shearing edge 263" being not parallel to the center axis of the outer tubular member. As shown in FIG. 10F, the window or axially extending recess W on the outer axial surface of the tubular member is trapezoid-shaped (shape of a truncated cone) as seen from the top. In the embodiment of the outer tubular member 264 shown in FIGS. 10H and 10I, the window or axially extending recess on the outer axial surface of the tubular member is configured so that the angle φ between the wall of the window and the outer axial surface is less than 90° (φ<90°) and the protrusion surface is winding as illustrated, and includes the first shearing edge 264' and the second shearing edge 264", with the second shearing edge 264" being not parallel to the center axis of the outer tubular member. As shown in FIG. 10H, the window or axially extending recess W on the outer axial surface of the tubular member is trapezoid-shaped (shape of a truncated cone) as seen from the top. The embodiments shown in FIGS. 10E-10I are configured so that the first shearing edge works like a blade and is well-suited to producing a relatively strong shearing force.

FIGS. 10J-10O illustrate yet further embodiments depicting different configurations of the shearing portions or shearing edges on the outer tubular member. Each of the embodiments shown in FIGS. 10J-10O is devoid of the radially inwardly directed protrusion associated with others of the above-described and illustrated embodiments of the outer tubular member. In the embodiment of the outer tubular member 265 shown in FIGS. 10J and 10K, the window W or axially extending recess on the outer axial surface of the outer tubular member is configured so that a 90° angle (φ=90°) exists between the wall of the window and the outer axial surface, and includes the first shearing edge 265' and the second shearing edge 265", with the second shearing edge 265" being parallel to the center axis of the outer tubular member. In the embodiment of the outer tubular member 266 shown in FIGS. 10L and 10M, the window or axially extending recess on the outer axial surface of the tubular member is configured so that the angle φ between the wall of the window and the outer axial surface is less than 90° (φ<90°), and includes the first shearing edge 266' and the second shearing edge, with the second shearing edge being not parallel to the center axis of the outer tubular member. In the embodiment of the outer tubular member 267 shown in FIGS. 10N and 10O, the window or axially extending recess on the outer axial surface of the tubular member is configured so that the angle ϕ between the wall of the window and the outer axial surface is less than 90° (ϕ<90°) and the surface is winding as illustrated, and includes the first shearing edge 267' and the second shearing edge, with the second shearing edge being not parallel to the center axis of the outer tubular member. Though the embodiments of the outer tubular member shown in FIGS. 10J-10O do not include a protrusion, the outer tubular member can still generate a shearing force. The recess W is configured to a side wall including the second shearing member, another side wall in head-on position of the side wall and a bottom surface. An area of the side wall is larger than an area of the other side wall. In this case, the outer tubular member may not have the protrusion.

Another aspect of the medical device disclosed here involves the medical device being configured to permit the use of a coated guidewire during rotation of the treatment member, and to permit the use of a single coated guidewire to both guide the treatment member to the treatment region and to perform the grinding operation during which the treatment member is rotated. This aspect of the medical device can be used together with the aspect of the medical device described above and illustrated in FIGS. 1-10D (shearing mechanism), or can be used by itself.

FIG. 11 illustrates a treatment member 502 configured to permit the use of a coated guidewire during rotation of the treatment member, and to permit the use of a single coated guidewire to both guide the treatment member to the treatment region and to perform the grinding operation during which the treatment member is rotated. The treatment member 502 shown in FIG. 11 is similar to the treatment member 102 shown in FIG. 4, except that the treatment member 502 shown in FIG. 11 lacks the outer tubular member 160 shown in FIG. 4 and includes a bearing mechanism as described below. But as noted above, the treatment member 502 shown in FIG. 11 can be modified to include the above-described outer tubular member 160 and associated shearing mechanism and other aspects described above and shown in FIGS. 1-10D.

The distal-most end portion 536 of the treatment member 502 is comprised of a distally tapering portion 542, an intermediate constant outer diameter portion 543 and a proximally tapering portion 544. The distally tapering portion 542, the intermediate constant outer diameter portion 543 and the proximally tapering portion 544 are similar to the distally tapering portion 142, the intermediate constant outer diameter portion 143 and the proximally tapering portion 144 described above.

The treatment member 502 shown in FIG. 11 is provided with a bearing mechanism that includes an inner tubular member 510. The inner tubular member 510 may be cylindrical in shape as illustrated and may be positioned in the lumen that extends throughout the axial extent of the treatment member 502. The distal-most end of the inner tubular member 510 may preferably be axially aligned with the distal-most end of the treatment member 502 or may be positioned distally beyond the distal-most end of the treatment member 502 as shown in FIG. 11. As described in more detail below, this arrangement helps ensure that the guidewire is not abraded (i.e., is not contacted by) the rotating treatment member 502 during operation. The axial extent of the inner tubular member 510 may be less than the axial extent of the treatment member 502. This shorter length of the inner tubular member 510 relative to the treatment member 502 helps reduce the friction between the inner tubular member 510 and the treatment member 502.

The inner tubular member 510 may be sized and positioned relative to the treatment member 502 so that the proximal-most end of the inner tubular member 510 is spaced distally from the distal-most end of the window 550 in the treatment member. This window 550 is similar to the window 150 shown in FIGS. 3 and 5.

The embodiment of the treatment member 502 shown in FIGS. 11 and 12 includes a bearing arrangement for facilitating relative rotation between the treatment member 502 and the inner tubular member 510. In this embodiment, the bearing arrangement is in the form of a plurality of balls or spheres 512. The balls 512 are positioned, relative to the axial direction (i.e., the left-to-right direction in FIGS. 11 and 12) at the larger diameter intermediate portion 543 of the treatment member 502.

To properly position, locate or seat the spheres 512 relative to the inner tubular member 510 and the treatment member 512, the outer periphery or outer surface of the inner tubular member 510 may be provided with a circumferential groove while the inner surface or inner periphery of the treatment member 502 includes several circumferentially spaced-apart recesses that each receive one of the balls 512. As shown in FIG. 13, the balls 512 may be located at the axial mid-point between the distal-most end of the inner tubular member 510 and the proximal-most end of the inner tubular member 510, and the axial midpoint of both the inner tubular member 510 and the balls 512 may be aligned with the axial midpoint of the intermediate constant outer diameter portion 543 of the treatment member 502.

The lumen 514 extending throughout the inner tubular member 510 may possess a constant inner diameter such as shown in FIG. 11. The lumen 514 in the inner tubular member 510 may be coaxial with the lumen 522 that extends through the drive shaft 520 and may be coaxial with the open end at the distal-most end (left end in FIG. 11) of the treatment member 502.

FIG. 13 illustrates another version of the inner tubular member 510' in which both the distal portion and the proximal portion of the inner tubular member 510' are tapered so that the lumen 514' in the tubular member 510' increases in size or cross-section toward the distal-most end of the tubular member 510' and so that the lumen 514' in the inner tubular member 510' increases in size toward the proximal-end of the tubular member 510'. The tapering inner diameter of the lumen 514' at the distal portion (the left end portion in FIG. 13) of the inner tubular member 510' helps reduce guidewire damage during use of the treatment member while the tapering inner diameter of the proximal portion of the lumen 514' (i.e., the right end in FIG. 13) helps facilitate insertion of the guidewire into the lumen 514' in the tubular member 510' from the handle side of the treatment member.

In the illustrated embodiment shown in FIGS. 11 and 12, more than half of the outer surface of each of the balls 512 is housed in the respective recess or hole in the treatment member 502.

The inner diameter of the tubular member 510 (i.e., the inner diameter of the constant inner diameter of the lumen 514 in the inner tubular member 510) may be equal to the inner diameter of the lumen 522 in the driveshaft 520 as shown in FIG. 11. The inner diameter of the constant inner diameter intermediate portion of the lumen 514' in the inner tubular member 510' may also be equal to the inner diameter of the lumen 522 in the driveshaft 520. It is also possible for the inner diameter of the constant inner diameter intermediate portion of the lumen 514' in the inner tubular member 510' to be smaller than the inner diameter of the lumen 522 in the driveshaft 520.

FIGS. 14A and 14B illustrate two alternative embodiments of the inner tubular member, each representing hybrid inner tubular members. The embodiment of the inner tubular member 610, shown in FIG. 14A includes a proximal portion 612 made of one material and a distal portion 614 made of a different material. In the illustrated embodiment of the inner tubular member 610, the proximal portion 612 is a constant outer diameter portion possessing a constant outer diameter throughout its length and the distal portion 614 is a tapering portion that gradually narrows in outer diameter toward the distal end.

In this embodiment, the proximal portion 612 of the inner tubular member 610 may be made of metal (examples include SUS304, SUS440C, SUS630) while the distal portion 614 may be made of polymer material (examples include polyolefin such as polyurethane, polyethylene or polypropylene, polyamides, polyesters such as polyethylene terephthalate, fluorine series such as PTFE Polymer, PEEK, polyimide, or combinations thereof). The proximal portion 612 of the inner tubular member 610 may include an axially extending projection 613 that is an integral part of the proximal portion 612 and that extends into a blind hole or recess in the distal portion 614. The axially extending projection 613 of the proximal portion 612 has a smaller outer diameter or outer size than the remainder of the proximal portion 612. The two portions 612, 614 of different materials are thus integrated or fixed together. The projection 613 can be fixed in the distal portion in any appropriate manner. The continuous circumferentially extending groove 616 that receives the balls 512 may be provided in the proximal portion 612 in this embodiment. A through hole or lumen 618 extends throughout the proximal portion 612, through the axially extending projection 613 and through the distal portion 614. This lumen or through hole 618 receives the guidewire during use of the medical device and during rotation of the he treatment member.

The embodiment of the tubular member 710 shown in FIG. 14B includes a proximal portion 712 at the proximal portion of the inner tubular member 710 and a distal portion 714 at the distal portion of the inner tubular member 710. The proximal portion 712 of the tubular member 710 is made of one material and the distal portion 714 is made of a different material. In this embodiment, the proximal portion 712 is a constant outer diameter portion possessing a constant outer diameter throughout its length and the distal portion 714 is a tapering portion that gradually narrows in outer diameter toward the distal end.

The proximal portion 712 of the inner tubular member 710 may be made of metal (examples include SUS304, SUS440C, SUS630) while the distal portion 714 may be made of polymer material (examples include polyolefin such as polyurethane, polyethylene or polypropylene, polyamides, polyesters such as polyethylene terephthalate, fluorine series such as PTFE Polymer, PEEK, polyimide, or combinations thereof). The distal portion 714 includes an axially extending projection 713 that is positioned in a hole in the proximal portion 712 and that may extend throughout the entire axial extent of the proximal portion 712. The axially extending projection 713 may be appropriately fixed in place in the proximal portion 712. The outer periphery of the metal portion 712 may be provided with the circumferential continuous groove 716 that receives the balls 512 forming the bearing arrangement. A through hole 718 extends throughout the polymer portion 714 as well as the entirety of the axially extending projection 713.

FIGS. 15 and 16 illustrate slightly different versions of the bearing arrangement. The embodiment of the inner tubular member 810 shown in FIG. 15 is similar to the embodiment depicted in FIGS. 11-13, except that only one of the ends of the lumen in the tubular member is tapered. In this illustrated embodiment, it is the distal end portion 812 that is tapered while the proximal end portion 814 possesses a constant inner diameter. It is of course also possible, if desired, to configure the proximal end portion of the lumen in the inner tubular member as a tapered portion while the distal end portion of the lumen possesses a constant inner diameter.

The embodiment of the inner tubular member 910 shown in FIG. 16 is a bush-type bearing arrangement that does not include the balls or spheres. Instead, the outer surface of the inner tubular member 910 is a constant outer diameter and is configured to rotate relative to the inner surface of the lumen in the treatment member. To axially maintain the position of the bush-type bearing arrangement represented by the inner tubular member 910 shown in FIG. 16, the proximal end of the inner tubular member 910 is configured as a hook portion. That is, the proximal end portion 914 of an inner tubular member 910 is an enlarged outer diameter portion 915 possessing an enlarged outer diameter relative to the outer diameter of the axially adjacent portion of the inner tubular member 910. This enlarged outer diameter portion or hook portion 915 fits into a similarly shaped annular recess or groove in the inner surface of the treatment member to prevent the bush-type bearing arrangement or inner tubular member 910 from falling out or becoming separated from the treatment member. In this embodiment, the inner tubular member 910 may be made of metal or polyolefin such as polyurethane, polyethylene or polypropylene, polyamides, polyesters such as polyethylene terephthalate, fluorine series such as PTFE Polymer, PEEK, polyimide, or combinations thereof.

Figure 18A:
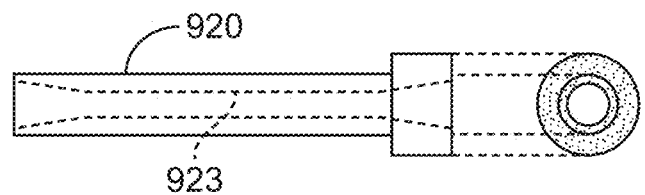

The embodiment of the inner tubular member 910 shown in FIG. 16 include a lumen that is a constant outer diameter along the entire axial extent of the inner tubular member 910. It is possible to taper the distal end portion and/or the proximal end portion of the lumen in the inner tubular member 910. In this regard, FIGS. 18A-18D illustrate various alternative embodiments for the inner tubular member. FIG. 18A illustrates an embodiment of the inner tubular member 920 similar to the version shown in FIG. 16, except that the lumen 923 passing through the inner tubular member 920 is tapered at both axial ends so that the inner diameter of the lumen 923 increases towards the axial ends of the inner tubular member 920.

Figure 18B:
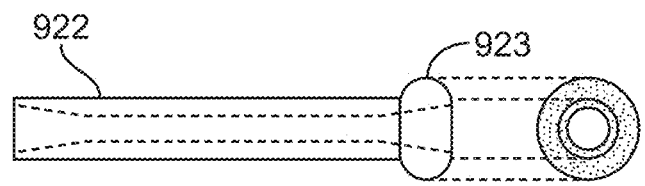

FIG. 18B illustrates another embodiment of the inner tubular member 922 that is the same as the embodiment shown in FIG. 18A, except that the enlarged outer diameter portion or hook portion 923 is rounded to reduce friction between the bush 922 and the inner surface of the treatment member.

Figure 18C:
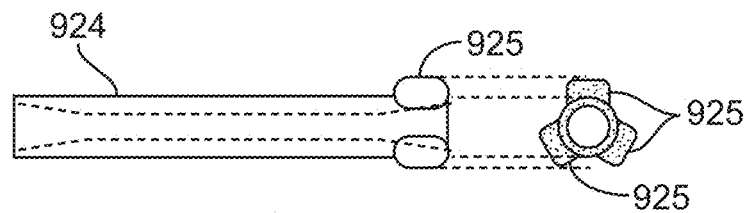

FIG. 18C illustrates an additional embodiment of the inner tubular member 924 that is quite similar to the embodiment shown in FIG. 18B, except that the enlarged outer diameter portion or hook portion 925 is comprised of several circumferentially spaced apart enlarged outer diameter portions 925 exhibiting a rounded configuration as shown. This arrangement may help reduce friction between the bush 924 and the inner surface of the treatment member.

Figure 18D:
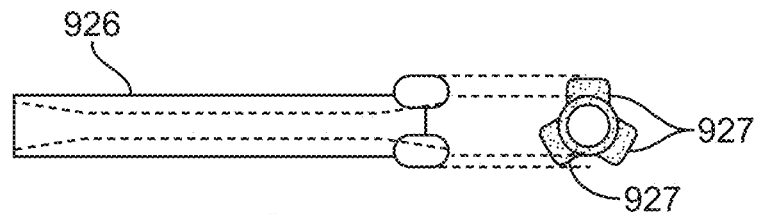

FIG. 18D illustrates a further embodiment of the inner tubular member 926 that is similar to the embodiment shown in FIG. 18C, except that the circumferentially spaced apart enlarged outer diameter portions 927 extend proximally beyond the remainder of the inner tubular member 927 as shown. This may help reduce friction between the bush 926 and the distal end of the drive shaft.

FIG. 19 depicts another version of the treatment member in which the inner tubular member 912 is a polymer-based tube (i.e., a tube or tubular member made of polymer-based material). An example of the polymer-based material is PTFE. This facilitates soft contact with the guidewire and reduced friction with the guidewire. The polymer material of which the inner tubular member 912 is made may thus differ from the material forming the treatment member which may be metal, and also differing from the material forming the drive shaft.

In this embodiment, the inner tubular member 912 is fixed relative to the treatment member 102 so that the tubular member 912 and the treatment member 102 move (e.g., rotate) together. According to the disclosed embodiment representing one example of the disclosed treatment member, the inner tubular member 912 is fixed relative to the treatment member 102 by virtue of the inner tubular member 912 being fixed to the treatment member 102. The inner tubular member 912 may be fixed to the treatment member 102' by any suitable manner such as glue or other suitable material. The relative fixation of the inner tubular member 912 and the treatment member 102 may also be achieved by virtue of the inner tubular member 912 being fixed to the drive shaft.

In this illustrated embodiment, the distal end portion of the inner tubular member 912 is positioned distally beyond the distal-most end of the treatment member 102. This thus helps prevent the guidewire from contacting the treatment member which may be made of metal. The proximal end of the tubular member 912 may be positioned on the distal side of the drive shaft 940. That is, the proximal end of the tubular member 912 may be located distally of the distal end of the drive shaft 940. The distal end of the drive shaft may have sharp edges and so this positioning helps avoid contact of the guidewire with the sharp edges, if any, of the drive shaft. Also, the drive shaft can be a helical single coil comprised of a round wire (i.e., a wire with a round cross-section). The inner surface of a helical single coil comprised of a wire with a round cross-section may also help avoid damage to the guidewire. In FIG. 19, the thicker dotted line represents the inner lumen of the treatment member while the thinner dotted line represents the inner lumen of the drive shaft and the tubular member.

The use of the medical device 100 may be as follows. The following discussion assumes the medical device includes both the outer tubular member providing the shearing forces and the inner tubular member providing the bearing arrangement. To begin, an incision is made in the living body to provide access to the living body, and then a guidewire is introduced into the living body and advanced toward the target region in the body lumen (e.g., the stenosis in a blood vessel). The distal end of the treatment member 102, positioned relative to the distal end of the outer sheath 116 as shown in FIG. 4, is advanced over the guidewire (an example of a guidewire is shown in FIGS. 17A and 17B) and is moved forward to position the treatment member 102, 502 at the treatment region (i.e., the place at which is located the substance S to be ground). The motor is then operated to rotate the treatment member at a high speed. The rotation speed of the treatment member may range from 5,000 rpm to 200,000 rpm, more preferably 10,000 rpm to 120,000 rpm.

The substance S to be ground in the body lumen is contacted by the rotating treatment member to thus grind the substance, resulting in debris D. The suction source or aspiration source connected to the interior of the outer sheath 116 by way of the aspiration tube 112 sucks the debris D toward the window(s) or through opening(s) 150 in the treatment member. During rotation of the treatment member, as the debris D is drawn toward the window(s) or through opening(s) 150 in the treatment member, the debris D is subjected to the shearing action described above by virtue of the interaction between the shearing surfaces or shearing edges of the outer tubular member 160 and the shearing surfaces or shearing edges of the of the treatment member. This thus reduces the size of the debris, helping to reduce possible choking of the aspiration port as the debris is sucked out of the living body, under the suction force of the suction source 111, by way of the lumen in the interior of the treatment member and the lumen in the outer sheath 116.

The inner tubular member 510, 610, 710, 810, 910 helps ensure that the high-speed rotating treatment member is able to rotate relative to the guidewire (and the inner tubular member) so that the high-speed rotating treatment member does not contact the guide wire and abrade or otherwise damage the guidewire.

The operation of the medical device with the inner tubular member 912 shown in FIG. 19 is generally the same, except that instead of the high-speed rotating treatment member rotating relative to the inner tubular member, the high-speed rotating treatment member rotates together with the inner tubular member 912, and the polymer material forming the inner tubular member 912 reduces harmful abrasion of the guidewire as the inner tubular member 912 and the treatment member rotate.

The detailed description above describes embodiments of a medical device and method for grinding substance from a body lumen representing examples of the inventive medical device and method disclosed here. The invention is not limited, however, to the precise embodiments and variations described. Various changes, modifications and equivalents can effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A medical device for treating a stenotic region in a body lumen in a living body, the medical device comprising:
   a rotatable tubular drive shaft;
   a treatment member positionable in the body lumen in the living body adjacent the stenotic region and possessing an outer grinding surface for grinding the stenotic region in the body lumen in the living body, the treatment member being connected to the drive shaft so that rotation of the drive shaft results in rotation of the treatment member, and the rotation of the treatment member causing the outer grinding surface of the treatment member to grind the stenotic region in the body lumen in the living body;
   the treatment member that rotates together with the rotatable tubular drive shaft possessing an axial extent, the treatment member including an axially extending lumen that extends throughout the axial extent of the treatment member;
   an inner tubular member possessing oppositely located distal-most and proximal-most ends, the inner tubular member including an axially extending lumen that extends throughout an axial extent of the inner tubular member so that the lumen opens to the distal end-most of the inner tubular member and to the proximal-most end of the inner tubular member to permit passage of a guidewire, at least a distal part of the inner tubular member being positioned in the lumen of the treatment member;

the treatment member that rotates together with the rotatable tubular drive shaft being rotatable relative to the inner tubular member, the treatment member that rotates together with the rotatable tubular drive shaft including a distal-most end portion and a proximal-most end portion, an entirety of the outer grinding surface of the distal-most end portion of the treatment member that rotates together with the rotatable tubular drive shaft being exposed so that the entirety of the outer grinding surface of the distal-most end portion of the treatment member is contactable with the stenotic region in the body lumen in the living body to grind the stenotic region;

the inner tubular member including an enlarged diameter portion that is enlarged relative to an axially adjacent part of the inner tubular member, the enlarged diameter portion possessing an outer diameter;

a portion of the lumen in the treatment member possessing an inner diameter smaller than the outer diameter of the enlarged diameter portion of the inner tubular member; and the enlarged diameter portion of the inner tubular member being positioned to contact the portion of the lumen in the treatment member that possesses the inner diameter smaller than the outer diameter of the enlarged diameter portion to limit axial movement of the inner tubular member relative to the treatment member.

2. The medical device according to claim 1, wherein a distal portion of the inner tubular member protrudes distally beyond a distal-most end of the treatment member.

3. The medical device according to claim 1, wherein the enlarged diameter portion of the inner tubular member is positioned closer to one of the distal-most end and the proximal-most end of the inner tubular member than the other of the distal-most end and the proximal-most end of the inner tubular member.

4. The medical device according to claim 1, wherein the enlarged diameter portion of the inner tubular member is positioned closer to proximal-most end of the inner tubular member than the distal-most end of the inner tubular member.

5. The medical device according to claim 1, wherein the enlarged diameter portion of the inner tubular member is positioned proximal of a distal portion of the inner tubular member.

6. The medical device according to claim 1, wherein the treatment member includes a tapering portion that tapers from a larger outer dimension to a smaller outer dimension, the smaller outer dimension being distal of the larger outer dimension.

7. A medical device for treating a stenotic region in a body lumen in a living body, the medical device comprising:
a treatment member positionable in the body lumen in the living body adjacent the stenotic region and possessing an outer surface for grinding the stenotic region in the body lumen in the living body;
a rotatable drive shaft connected to the treatment member and connectable to a motor so that operation of the motor results in rotation of the drive shaft and the treatment member to grind the stenotic region in the body lumen in the living body;
a tubular member that includes an axially extending lumen that extends throughout an axial extent of the tubular member so that the lumen opens to opposite ends of the tubular member, a distal part of the tubular member being positioned in a lumen of the treatment member so that the distal part of the tubular member and the treatment member axially overlap one another;
the treatment member including a distal-most end portion and a proximal-most end portion, an entirety of the outer surface of the distal-most end portion of the treatment member being exposed so that the entirety of the outer surface of the distal-most end portion of the treatment member is contactable with the stenotic region in the body lumen in the living body to grind the stenotic region, the distal-most end portion of the treatment member that is exposed being rotatable relative to the tubular member;
the tubular member including a portion possessing an outer diameter; and
a part of the lumen in the treatment member possessing an inner diameter smaller than the outer diameter of the portion of the tubular member to limit relative axial movement between the tubular member and the treatment member by virtue of contact between the portion of the tubular member and the part of the lumen in the treatment member.

8. The medical device according to claim 7, wherein a distal portion of the tubular member protrudes distally beyond a distal-most end of the treatment member.

9. The medical device according to claim 7, wherein the portion of the tubular member is positioned closer to one of the opposite ends of the tubular member than the other.

10. The medical device according to claim 7, wherein the portion of the tubular member is positioned closer to a proximal end of the tubular member than a distal end of the tubular member.

11. The medical device according to claim 7, wherein the portion of the tubular member is positioned proximal of a distal portion of the tubular member.

12. The medical device according to claim 7, wherein the axially extending lumen in the tubular member includes a distal portion possessing a constant inner diameter.

13. The medical device according to claim 7, wherein the drive shaft includes a lumen opening to opposite axial ends of the drive shaft.

14. A medical device for treating a stenotic region in a living body comprising:
a drive shaft connectable to a motor so that operation of the motor results in rotation of the drive shaft;
a treatment member connected to a distal portion of the drive shaft so that the treatment member rotates together with rotation of the drive shaft, the treatment member including an outer surface and an inner edge, the treatment member that rotates together with the drive shaft including a distal-most end portion;
an inner tubular member positioned in the treatment member, the inner tubular member including an enlarged outer diameter portion and an axially extending lumen that extends throughout an axial extent of the inner tubular member so that the lumen opens to a distal-most end of the inner tubular member and to a proximal-most end of the inner tubular member to permit positioning a guidewire in the lumen, the enlarged outer diameter portion of the inner tubular member having an outer diameter larger than a portion of the inner tubular member immediately axially adjacent the enlarged outer diameter portion of the inner tubular member, the enlarged outer diameter portion of the inner tubular member being positioned in the treatment member;

the treatment member that rotates together with the drive shaft being rotatable relative to the inner tubular member;

an entirety of the outer surface of the distal-most end portion of the treatment member that rotates together with the drive shaft being exposed so that the entirety of the outer surface of the distal-most end portion of the treatment member is contactable with the stenotic region in the living body to grind the stenotic region; and the inner tubular member being limited in axial movement in a distal direction relative to the treatment member by virtue of the enlarged outer diameter portion of the inner tubular member engaging the inner edge of the treatment member.

15. The medical device according to claim 14, wherein a distal portion of the inner tubular member protrudes distally beyond a distal-most end of the treatment member.

16. The medical device according to claim 14, wherein the enlarged outer diameter portion of the inner tubular member is positioned closer to the proximal-most end of the inner tubular member than the distal-most end of the inner tubular member.

17. The medical device according to claim 14, wherein the enlarged outer diameter portion of the inner tubular member is positioned closer to one of the distal-most end and the proximal-most end of the inner tubular member than the other of the distal-most end and the proximal-most end of the inner tubular member.

18. The medical device according to claim 14, wherein the enlarged outer diameter portion of the inner tubular member is positioned proximal of a distal portion of the inner tubular member.

19. The medical device according to claim 14, wherein the drive shaft includes an axially extending lumen extending through an entire axial extent of the drive shaft.

20. The medical device according to claim 14, wherein the axially extending lumen in the inner tubular member includes a distal portion possessing a constant inner diameter.

* * * * *